(12) United States Patent
Ravikumar

(10) Patent No.: US 8,617,144 B2
(45) Date of Patent: Dec. 31, 2013

(54) VENOUS CLOSURE CATHETER AND METHOD FOR SCLEROTHERAPY

(76) Inventor: Sundaram Ravikumar, Briar Cliff Manor, NY (US)

( * ) Notice: Subject to any disclaimer, the term of this patent is extended or adjusted under 35 U.S.C. 154(b) by 150 days.

(21) Appl. No.: 13/081,827

(22) Filed: Apr. 7, 2011

(65) Prior Publication Data

US 2012/0022422 A1    Jan. 26, 2012

Related U.S. Application Data

(60) Provisional application No. 61/341,921, filed on Apr. 7, 2010, provisional application No. 61/342,368, filed on Apr. 13, 2010.

(51) Int. Cl.
*A61B 17/00* (2006.01)

(52) U.S. Cl.
USPC ............................................. 606/1; 606/159

(58) Field of Classification Search
USPC .............. 606/159, 169, 170, 171, 178, 180, 1
See application file for complete search history.

(56) References Cited

U.S. PATENT DOCUMENTS

| | | | | |
|---|---|---|---|---|
| 4,465,072 A | * | 8/1984 | Taheri | 606/159 |
| 5,738,109 A | * | 4/1998 | Parasher | 600/569 |
| 5,925,055 A | * | 7/1999 | Adrian et al. | 606/159 |

* cited by examiner

*Primary Examiner* — Michael A. Brown
(74) *Attorney, Agent, or Firm* — Edwards Wildman Palmer LLP; Scott D. Wofsy; Brian S. Matross

(57) ABSTRACT

A venous closure catheter is disclosed for performing sclerotherapy which includes an elongated catheter body having opposed proximal and distal end portions, a fluid delivery lumen and a guidewire lumen. A plurality of discharge apertures are associated with the distal end portion of the catheter body and communicate with the fluid delivery lumen for delivering a sclerosing solution into the saphenous vein. A circumferential flange is positioned on an exterior surface of the catheter body proximal to the discharge apertures, which has a plurality of projections formed thereon for traumatizing the inner wall of the saphenous vein upon removal of the catheter body therefrom to promote closure of saphenous vein after sclerotherapy. A compression apparatus is disclosed for providing therapeutic pressure subsequent to sclerotherapy. The compression apparatus includes first and second wraps for providing compression of an upper leg, and the lower leg and foot, respectively.

21 Claims, 14 Drawing Sheets

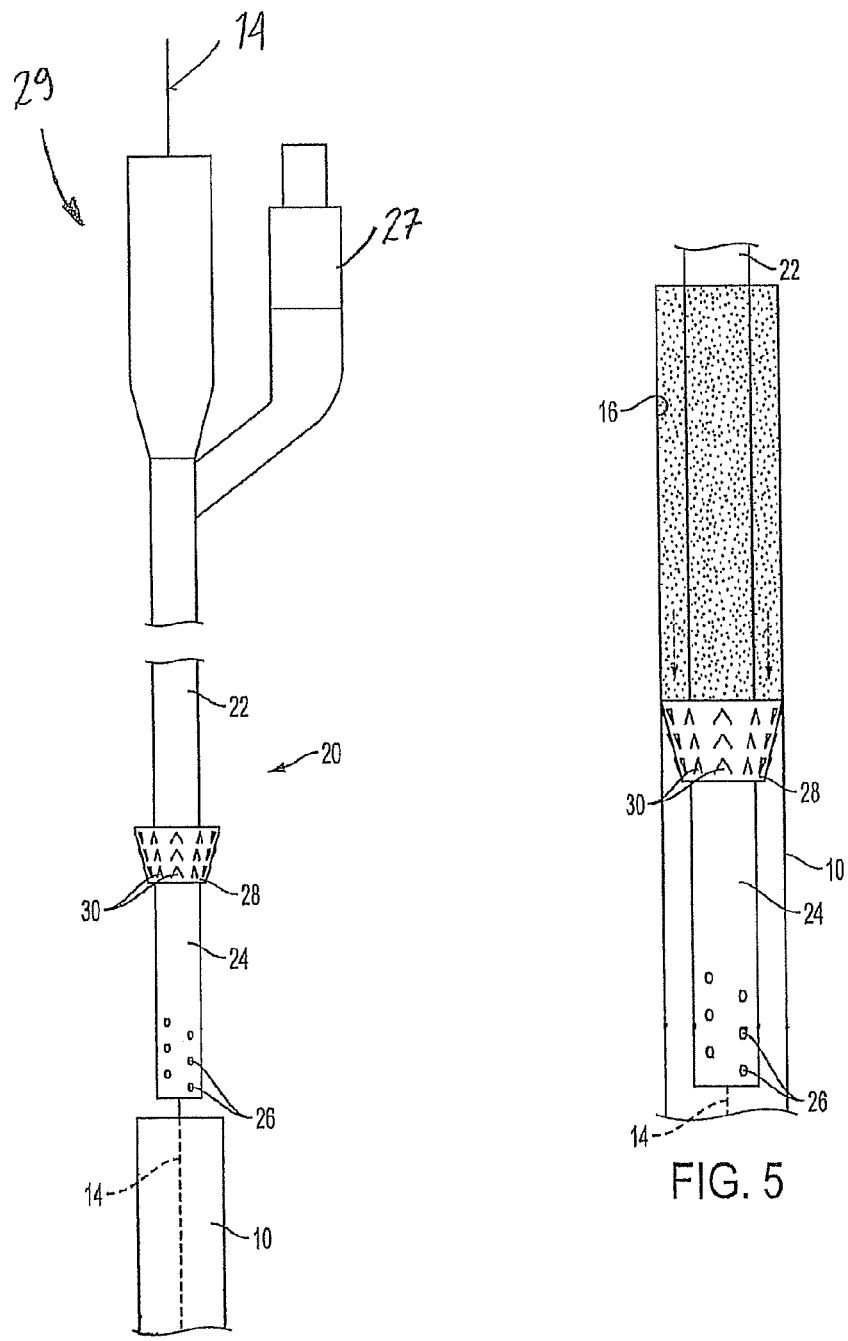

VENOUS CLOSURE CATHETER AND METHOD FOR SCLEROTHERAPY

CROSS-REFERENCE TO RELATED APPLICATIONS

This application claims priority to U.S. Provisional Patent Application Ser. Nos. 61/341,921 filed on Apr. 7, 2010 and 61/342,368 filed on Apr. 13, 2010. The entire contents of these applications are incorporated herein by this reference.

BACKGROUND OF THE INVENTION

1. Field of the Invention

The subject invention is directed generally to a venous catheter, and more particularly, to a venous catheter and method for performing sclerotherapy to treat varicose veins or spider veins by delivering a sclerosing solution into the saphenous vein, subsequently abrading the inner wall of the blood vessel upon removal of the catheter from the vein to promote venous closure, and using a compression apparatus to provide therapeutic pressure post-operatively.

2. Background of the Related Art

Chemical occlusion, also known as sclerotherapy, is a procedure used to treat blood vessels or vessel malformations, wherein a sclerosing solution is injected into the vessels, which makes the unwanted veins shrink and then dissolve over a period of weeks, as the body naturally absorbs the treated vein. Sclerotherapy is often used to eliminate large spider veins (telangiectasiae) and smaller varicose leg veins.

During a treatment procedure, sclerosing solution is injected into the abnormal veins of the involved leg. The patient's leg is then compressed with either stockings or bandages that they wear usually for two weeks after treatment. Complications, while rare, include venous thromboembolism, visual disturbances, allergic reaction, thrombophlebitis, skin necrosis, and hyperpigmentation. If the sclerosing agent is injected properly into the vein, there is no damage to the surrounding skin, but if it is injected outside the vein, tissue necrosis and scarring can result. Most complications occur due to an intense inflammatory reaction to the sclerotherapy agent in the area surrounding the injected vein. In addition, there are systemic complications that are now becoming increasingly understood. These occur when the sclerosing solution travels through the veins to the heart, lung and brain.

Apparatus and methods are also known for performing sclerotherapy using a catheter, as disclosed for example in U.S. Pat. No. 6,726,674, the disclosure of which is incorporated herein by reference in its entirety. When the catheter is deployed in blood vessels, an inflatable member sealingly engages the interior walls of the blood vessel, establishing an isolated vessel segment to facilitate localized introduction of a sclerosing agent. Upon collapse of the inflatable member, the sclerosing agent is also withdrawn from the blood vessel. Over time, the treated vessel segment will shrink and then dissolve, as the body naturally absorbs the treated vein.

It would be beneficial to provide a venous catheter for delivering a sclerosing agent into a targeted vein that is configured to prohibit the migration of the sclerosing solution during treatment of the vein and which is also adapted to enhance the closure of the vein walls following sclerotherapy treatment.

SUMMARY OF THE INVENTION

The subject invention is directed to a venous closure catheter for performing ultrasound guided sclerotherapy which includes, among other things, an elongated catheter body having opposed proximal and distal end portions and at least one interior lumen, aperture means associated with the distal end portion of the catheter body and communicating with an interior lumen of the catheter body for delivering a sclerosing solution into the saphenous vein, and abrading means operatively positioned on the exterior of the catheter body proximal to the aperture means for abrading or otherwise traumatizing the inner wall of the saphenous vein upon removal of the catheter body therefrom to promote closure of saphenous vein after sclerotherapy.

Preferably, the aperture means is a plurality of fluid delivery ports formed in the distal end portion of the catheter body, although alternative features may be employed. Preferably, the abrading means is a circumferential flange having a plurality of projections adapted and configured to abrade the inner wall of the saphenous vein. It is envisioned that the flange has a generally frusto-conical configuration with a base oriented toward the proximal end portion of the catheter body and each projection has a barb-shaped configuration with a point that is oriented toward the proximal end portion of the catheter body. It is also envisioned that the flange may be adapted and configured for selective positioning along the length of the catheter body.

The subject invention is also directed to a method for performing sclerotherapy that includes the steps of introducing an elongated venous catheter into the saphenous vein, delivering a sclerosing solution into the saphenous vein through a distal end portion of the venous catheter, and abrading or otherwise traumatizing the inner wall of the saphenous vein upon removal of the venous catheter from the saphenous vein.

Preferably, the method further includes the steps of dividing the saphenous vein a short distance below the saphenofemoral junction, percutaneously introducing a guidewire into the saphenous vein at a location proximate the ankle and advancing the guidewire toward the divided end of the saphenous vein. In such a case, the step of introducing the venous catheter into the saphenous vein includes the step of guiding the introduction of the venous catheter along the guidewire from the divided end of the saphenous vein.

The subject invention is also directed toward a method of providing post operative pressure to the leg using a compression apparatus. In conjunction with performing the methods of sclerotherapy described herein, the method includes the step of providing post operative pressure to the leg containing the abraded saphenous vein. The method may further comprise the step of encircling the leg with a compression apparatus. In one embodiment, the step of encircling the leg with the compression apparatus further comprises the step of encircling at least an upper portion of the leg with a first wrap member. In another embodiment, the step of encircling the leg with the compression apparatus further comprises the step of encircling a lower portion of the leg and foot with a second wrap member. In yet another embodiment, the method of the subject invention further comprises the step of inflating a continuous chamber within a material of the compression apparatus. The method may further comprise the step of measuring pressure supplied to the leg by the inflated compression apparatus. The method may further comprise the step of securing the first wrap member about the upper portion of the leg using an adjustable strap around a patient's waist.

These and other aspects of the venous closure catheter of the subject invention will become more readily apparent from the following description taken in conjunction with the drawings.

BRIEF DESCRIPTION OF THE DRAWINGS

So that those having ordinary skill in the art to which the subject invention pertains will more readily understand how to make and use the female connector of the subject invention, preferred embodiments thereof will be described in detail hereinbelow with reference to the drawings, wherein:

FIG. 4 shows the guided introduction of the venous closure catheter of the subject invention into the divided saphenous vein;

FIG. 5 shows the transvenous placement of the venous closure catheter of the subject invention through the saphenous vein;

DETAILED DESCRIPTION OF THE PREFERRED EMBODIMENTS

1. Venous Closure Catheter Apparatus and Method

Figure 1A:
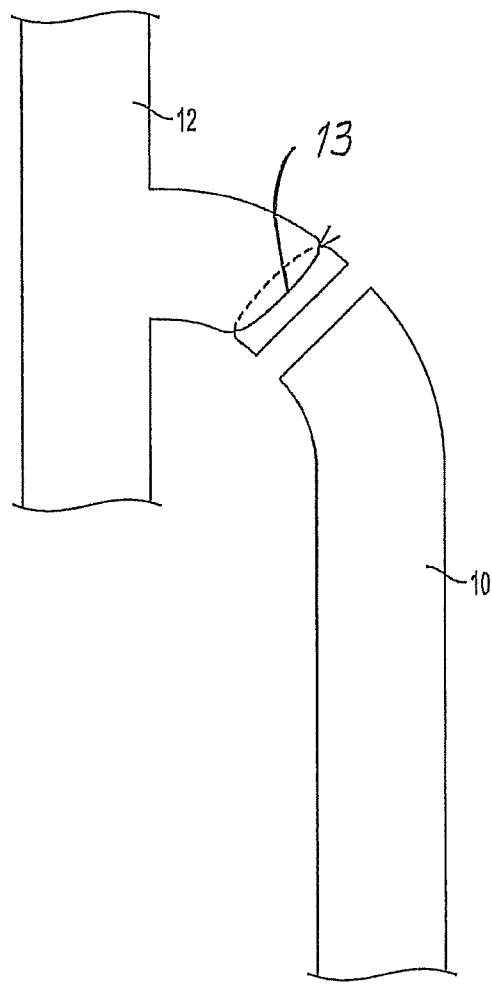
FIG. 1A is a schematic representation of the ligation of the saphenous vein below the sapheno-femoral junction to facilitate a sclerotherapy treatment within the long saphenous vein.

Referring now to the drawings wherein like reference numerals identify similar structural elements of the venous catheter of the subject invention, there is illustrated in FIG. 1A a schematic representation of the greater saphenous vein 10 of the leg, divided and freed a short distance below the sapheno-femoral junction 12, to facilitate sclerotherapy treatment utilizing the venous closure catheter of the subject invention, described in detail below. At such a time, the divided end of the sapheno-femoral junction, above the ligation is tied-off with one or more sutures 13.

Figure 1B:
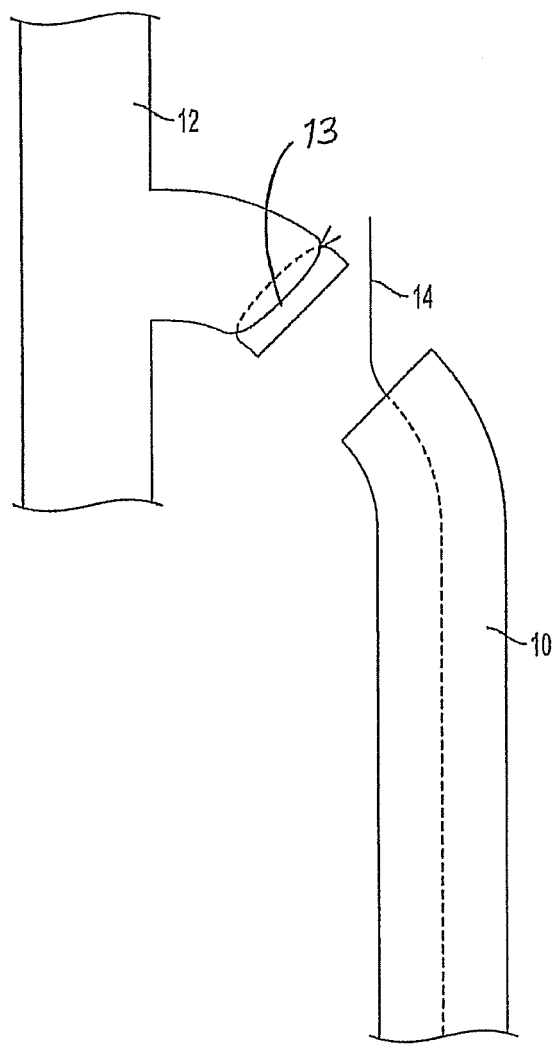
FIG. 1B shows the positioning of a guidewire in the divided saphenous vein, which is introduced percutaneously from the ankle.

Referring to FIG. 1B, there is shown a guidewire 14 for guiding the transvenous introduction of the venous catheter of the subject invention into the divided saphenous vein 10. In accordance with a preferred embodiment of the subject invention, the guidewire 14 is percutaneously introduced into the saphenous vein 10 from a location proximate the ankle and subsequently advanced toward the divided end of the saphenous vein where it is grasped and retained by the practitioner.

Figure 2:
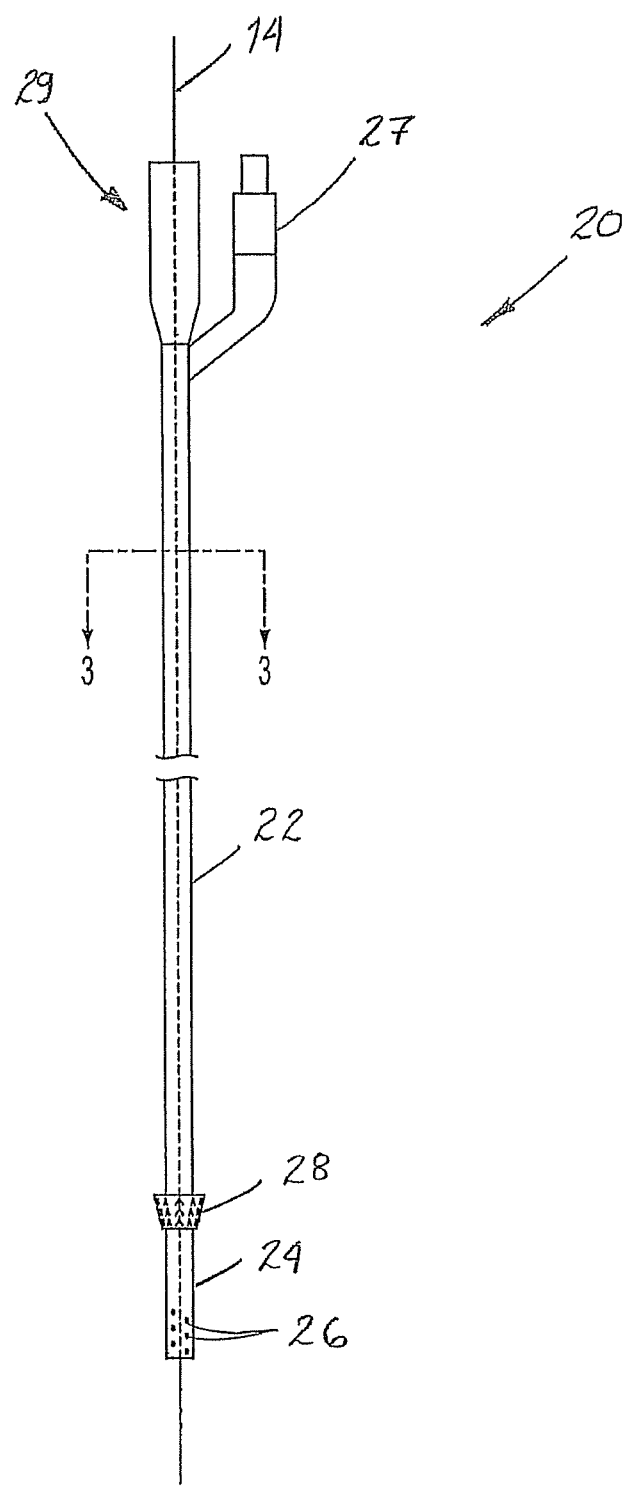
FIG. 2 is a plan view of a preferred embodiment of the venous closure catheter of the subject invention.

Referring now to FIG. 2, there is illustrated the venous closure catheter of the subject invention, which is designated generally by reference numeral 20. Venous catheter 20 includes an elongated catheter body 22 formed from a soft or otherwise flexible medical grade polymer, such as, for example, Polyurethane, Tecothane, Pebax, C-Flex or Silicone. The flexible catheter body 22 is preferably provided in various lengths to accommodate different anatomy (e.g., 30 to 60 centimeters in length) and has an outer diameter of about between 4 F and 5 F.

Figure 3:
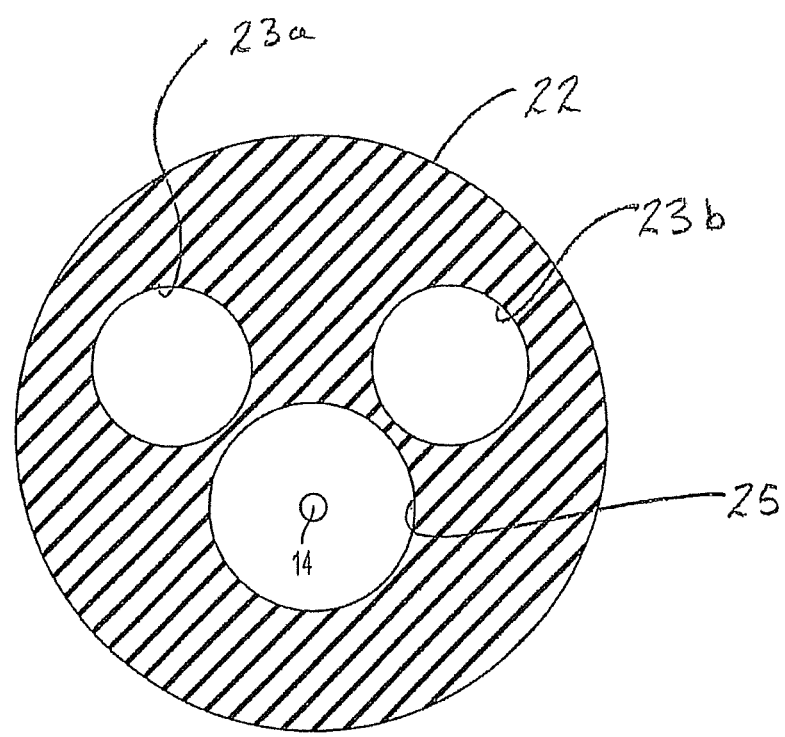
FIG. 3 is a cross-sectional view of the venous closure catheter taken along line 3-3 of FIG. 2, showing the interior lumens thereof.

Referring to FIG. 3, catheter body 22 includes one or more interior lumens 23a, 23b to facilitate the delivery of sclerosing solution or other media into a targeted vein section. In addition, at least one interior lumen 25 is provided to accommodate the passage of guidewire 14 during the transvenous introduction and removal of catheter 20. The interior lumens communicate with conventional fittings 27 operatively associated with the proximal end portion 29 of the catheter body 22.

Referring back to FIG. 2, the distal end portion 24 of catheter body 22 includes a plurality of apertures or ports 26 that are in fluid communication with one or both of the interior fluid delivery lumens 23a, 23b provided within catheter body 22. The apertures 26 are adapted and configured to introduce or otherwise deliver a sclerosing solution into the saphenous vein 10 during a sclerotherapy procedure. Alternatively, the distal end portion 24 of catheter body 22 can be open-ended to serve as a fluid delivery port. In such an instance, one or both of the fluid delivery lumens 23a, 23b would communicate directly with the open distal end of the catheter body 22.

Figure 8:
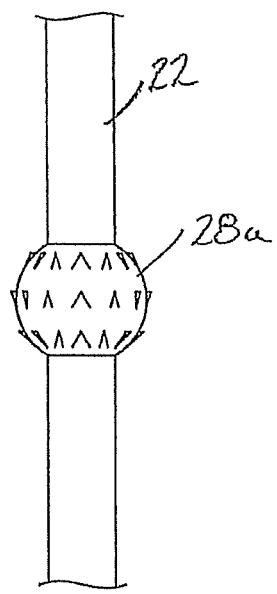
FIGS. 8 and 9 show alternate embodiments of the abrading feature of the venous closure catheter of the subject invention.
Figure 9:
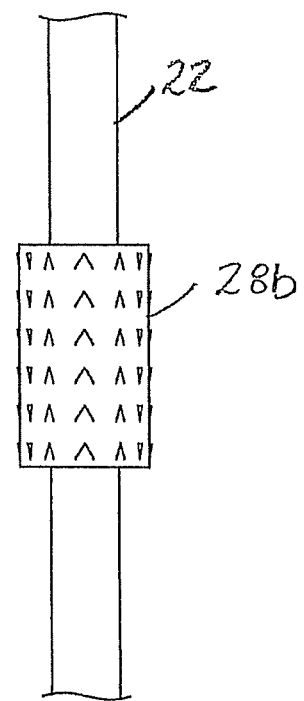

With continuing reference to FIG. 2, venous closure catheter 20 also includes a circumferential flange 28 spaced from the distal end of the catheter body 22, proximal to the fluid discharge apertures 26. The circumferential flange 28 preferably has a frusto-conical shape to ease transvenous introduction of the catheter body 22. However, those skilled in the art should readily appreciate that the flange 28 can have a different shape than frusto-conical without departing from the spirit or scope of the subject disclosure. For example, as shown in FIG. 8 it is envisioned that the circumferential flange 28a could be circular or ovoid in shape, or as shown in FIG. 9, the flange 28b could be cylindrical or annular in shape.

With continuing reference to FIG. 2 in conjunction with FIG. 4, the circumferential flange 28 is provided with a plurality of spaced protuberances or projections 30. The projections 30 are preferably barb-shaped and are oriented in rows with the pointed edges facing toward the proximal end of the catheter body 22, and away from the distal end portion 24. By orienting the projections 30 in this manner, during transvenous introduction of the venous catheter 20 into the saphenous vein 10, the projections 30 do not affect or other traumatize the vessel wall 16, as illustrated in FIG. 5.

Figure 6:
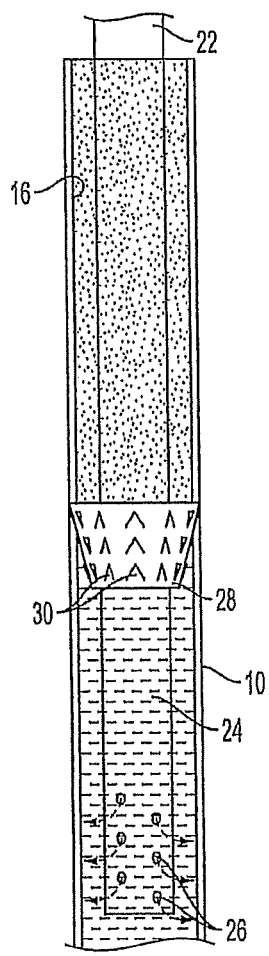
FIG. 6 shows introduction of sclerosing solution into the saphenous vein from the distal end portion of the venous catheter of the subject invention.

When the distal end portion 24 of catheter body 22 has reached the treatment site within the saphenous vein 10, as shown in FIG. 6, the sclerosing solution is delivered into the blood vessel through the plurality apertures 26. Thereupon, the sclerosing solution works to close and shrink the saphenous vein. During treatment, the circumferential flange 28 functions to limit or otherwise prohibit the migration of the sclerosing solution from the treatment site.

Figure 7:
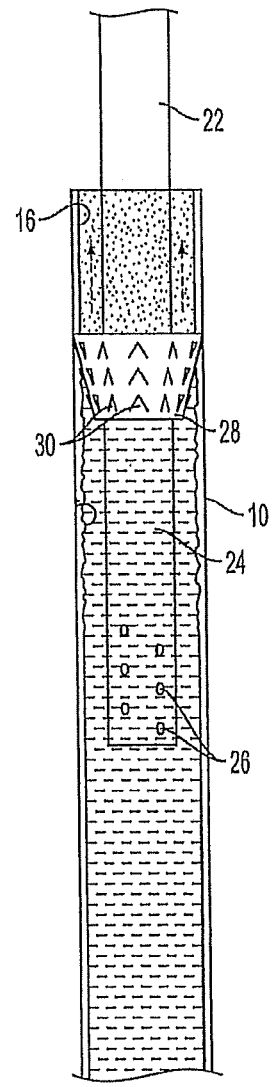
FIG. 7 shows the removal of the venous closure catheter from the saphenous vein after sclerotherapy, wherein the interior walls of the saphenous vein are abraded by the catheter during removal to promote vessel closure.

Referring to FIG. 7, when the venous closure catheter 10 is withdrawn or otherwise removed from the saphenous vein 10 after sclerotherapy treatment, the barb-like projections 30 on circumferential flange 28 abrade or otherwise traumatize the interior wall 16 of the saphenous vein 10. By abrading the vein wall 16 vessel closure is further promoted, enhancing the effect of the sclerosing solution. After the venous catheter 20 has been removed from the saphenous vein 10, the dissected free end of the vein is tied off and the entrance wound adjacent the sapheno-femoral junction is closed.

It is envisioned that the circumferential flange 28 can be fixedly attached to the catheter body 20 at a desired location relative to the apertures 26 in the distal end portion 24, or it could be adapted and configured for selective placement at a desired location along the length of the catheter body 22 prior to vascular introduction.

2. Method for Providing Post-Operative Pressure Using Compression Apparatus

The subject invention is also directed to methods for supplying pressure post-operatively using a compression apparatus. Following sclerotherapy treatment of the saphenous vein, for example, the compression apparatus of the subject invention may be used to provide therapeutic pressure to the upper leg and lower leg and foot in order to promote circulation and healing. The features of the upper leg wrap and the lower leg and foot wrap and methods associated therewith will be discussed in turn.

Figure 10A:
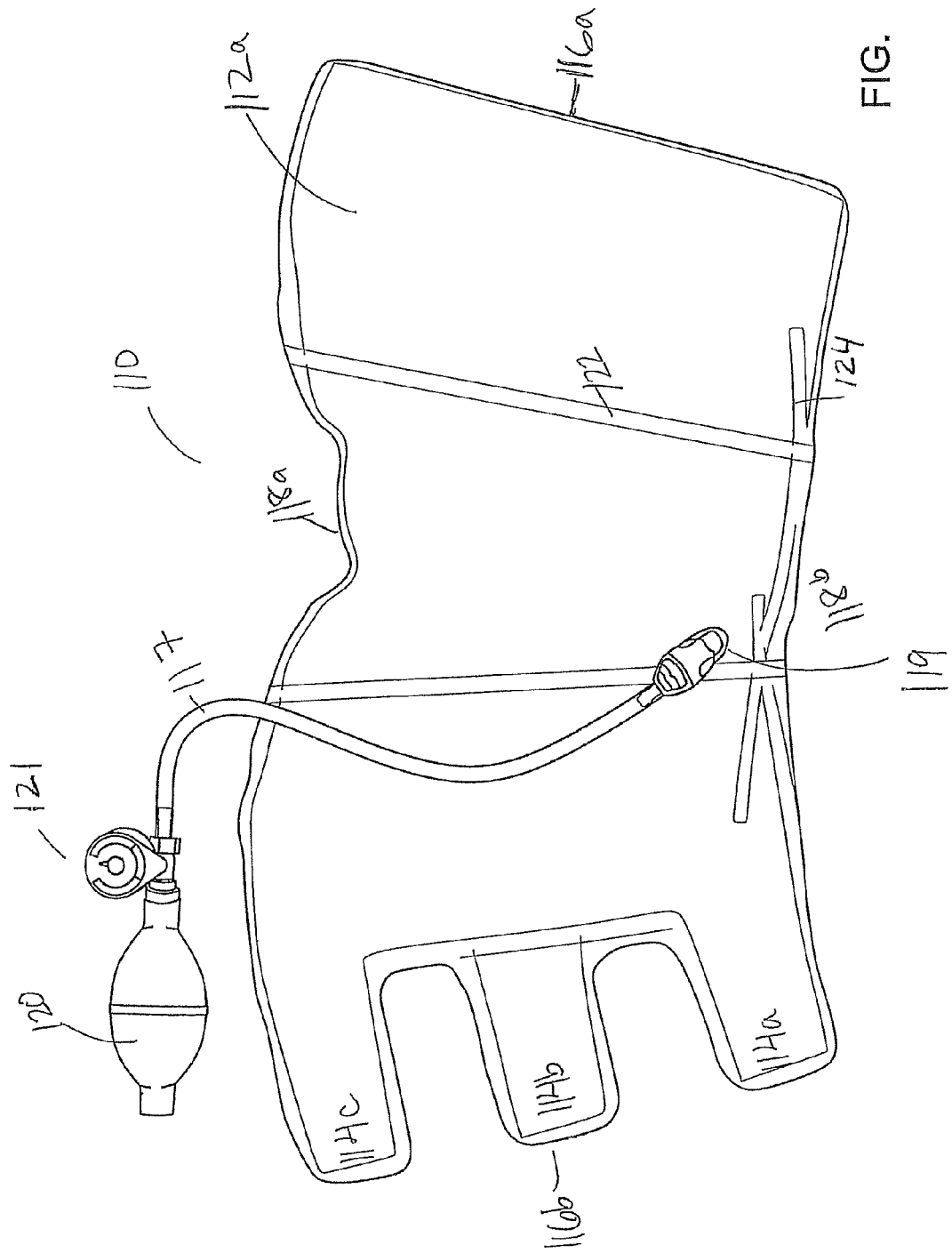
FIG. 10A is a perspective view of the exterior surface of an exemplary upper leg wrap according to the subject invention illustrated in an unwrapped state.

Referring now to FIG. 10A, an exemplary embodiment of an upper leg wrap 110 according to the subject invention is shown. The upper leg wrap 110 is shown in an unwrapped state having an exterior surface 112a. A user applies the upper leg wrap 110 by encircling the thigh in order to supply compression thereto. The exterior surface 112a and interior surface 112b of the upper leg wrap 110 are joined along common peripheral edges of the upper leg wrap 110 to form a chamber. The exterior surface 112a and interior surface 112b are both made of non-elastic materials, which do not stretch when inflated, in order to facilitate localized compression of the treatment site. As shown in FIG. 10A, the upper leg wrap 110 is also manufactured with a number of stitched darts 122 and gathers 124 which are strategically placed to contour the upper leg wrap 110 around the thigh. The upper leg wrap 110 may also include a permanent or detachable pressure gauge 121, such as a manometer, which may be capable of being detached using a connector at the inlet port 119. A pump 120, for example, a manual or electric pump, may also provided for pumping air into the inflatable chamber through an optional tube 117.

Figure 10B:
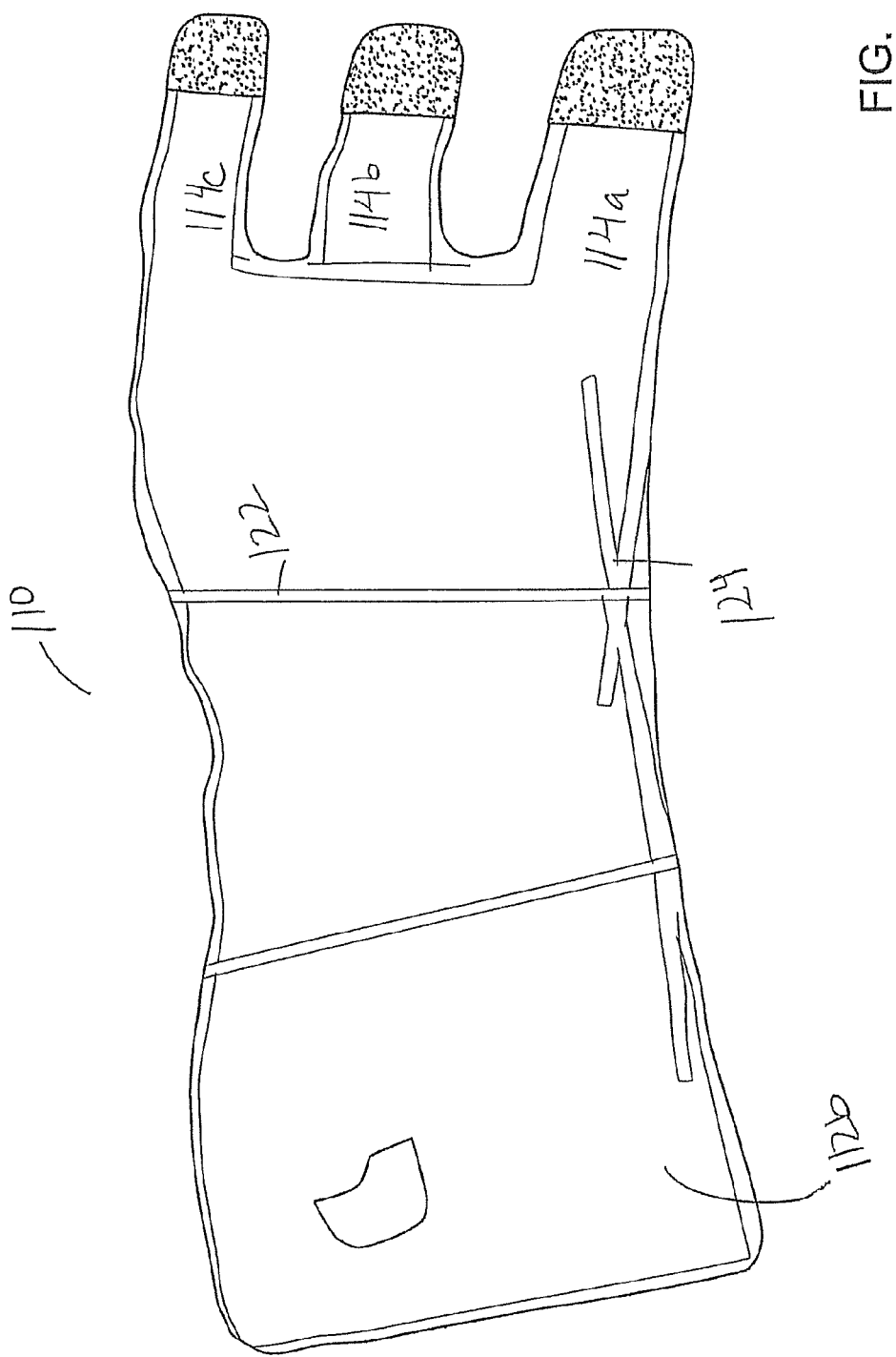
FIG. 10B is a perspective view of the interior surface of the upper leg wrap illustrated in an unwrapped state.

Referring now to FIG. 10B, upper leg wrap 110 of FIG. 10A is illustrated in an unwrapped state having interior surface 112b. The upper leg wrap 110 may be attached to a patient's upper leg 111, by encircling the upper leg 111 and attaching the upper leg wrap 110 to itself along the vertical peripheral edges 116a and 116b using a number of connecting structures. For example, three hook and loop fastening tabs, such as connecting tabs 114a, 114b, and 114c, may be provided to connect the opposing vertical peripheral edges 116a and 116b of the upper leg wrap 110 securely about the upper leg 111. Buckles, straps, snaps or other known structures may also be used to secure the upper leg wrap 110 around the patient's upper leg 111. The number and position of the connecting tabs 114a, 114b, 114c, may be selected based on the anatomical dimensions of the patient's upper leg 111 in order to reduce bunching, sagging and patient discomfort.

Figure 11A:
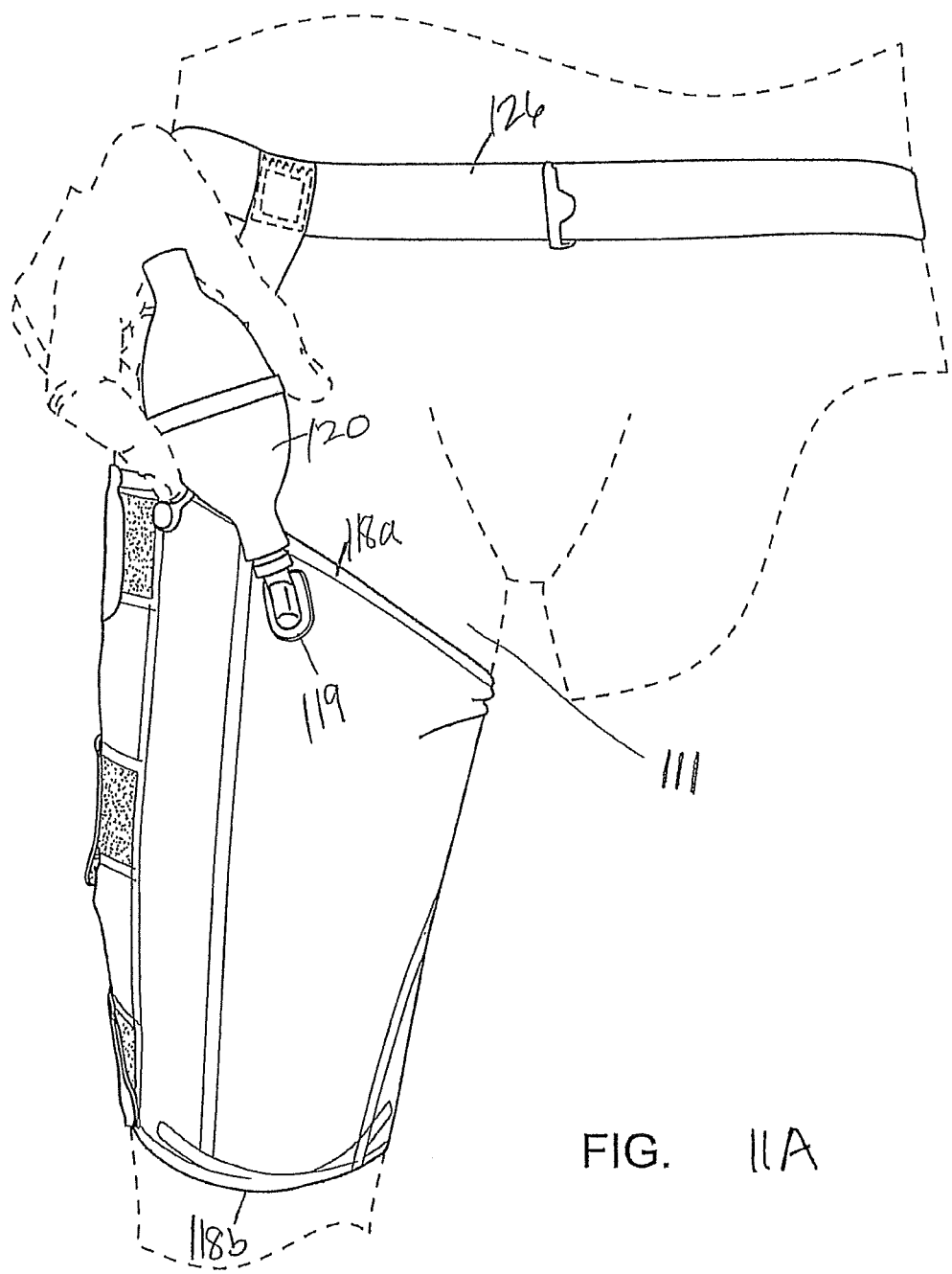
FIG. 11A is a perspective view of an upper leg wrap encircled around the upper leg and further secured to the upper leg using an optional adjustable belt around the patient's waist, the upper leg wrap being inflated using a detachable manual pump.
Figure 11B:
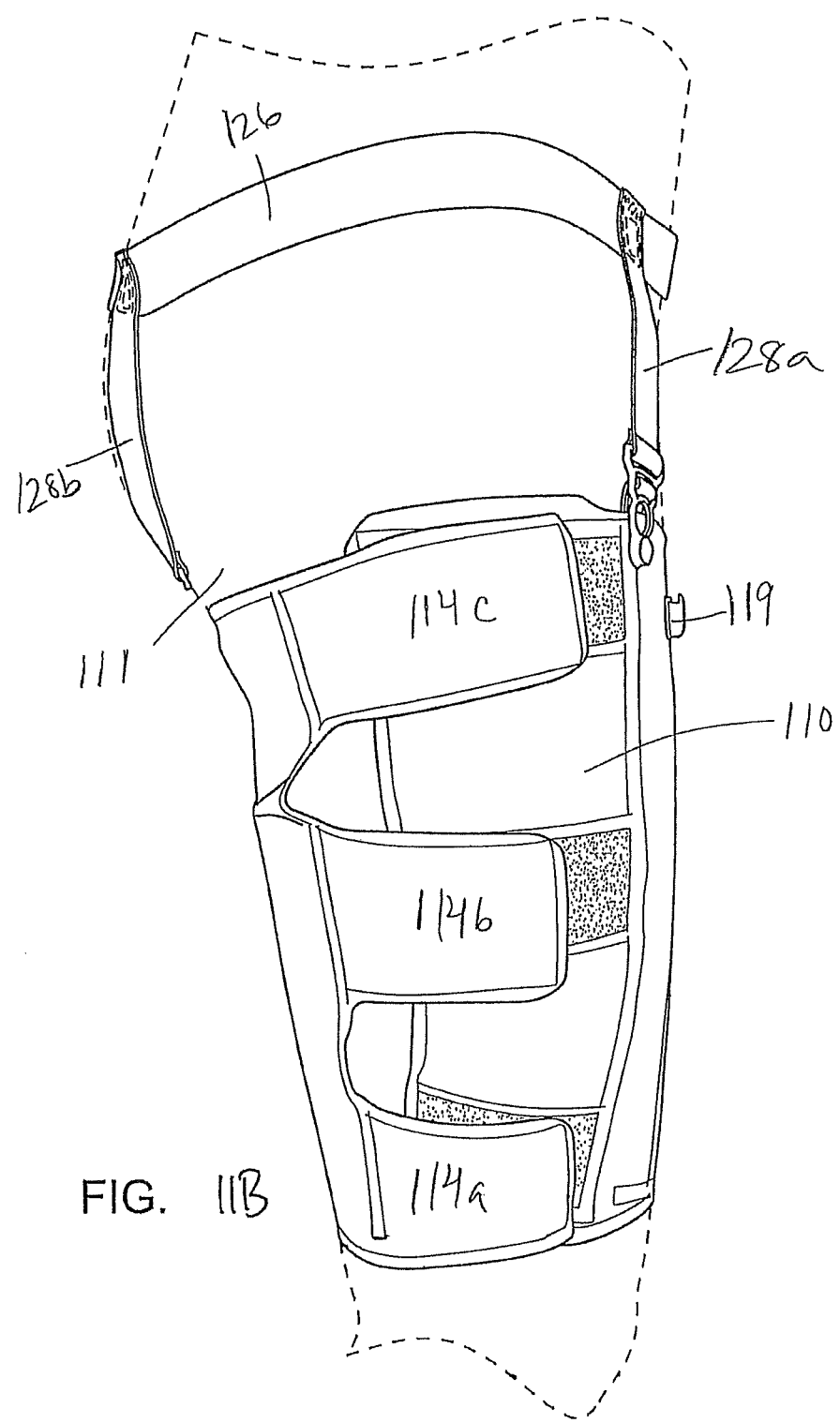
FIG. 11B is a side view of the upper leg wrap of FIG. 11A, the manual pump having been detached.

Referring now to FIGS. 11A and 11B, at a horizontal proximal end 118a, opposite the distal end 118b located towards the knee, an optional garter or adjustable belt 126 may be provided to further secure the upper leg wrap 110 in place. The adjustable belt 126 may be worn around the waist and connected to the upper leg wrap 110 using expandable connecting straps 128a and 128b. The number and placement of the expandable connecting straps 128a, 128b may also be altered to accommodate the patient's anatomical dimensions.

Referring now to FIG. 12A, an exemplary embodiment of a lower leg and foot wrap 130 according to the subject invention is illustrated in an unwrapped state. The lower leg and foot wrap 130 includes two portions, an upper portion 132 and a lower portion 134. The upper portion 132 is adapted and configured to supply compression of a patient's lower leg 142, whereas the lower portion 134 is adapted and configured to supply compression of a patient's foot 148. In one embodiment, the upper portion 132 and lower portion 134 are provided as one continuous piece of inflatable material, as shown in FIG. 112A. However, the upper portion 132 and the lower portion 134 may also be provided separately.

Figure 12:
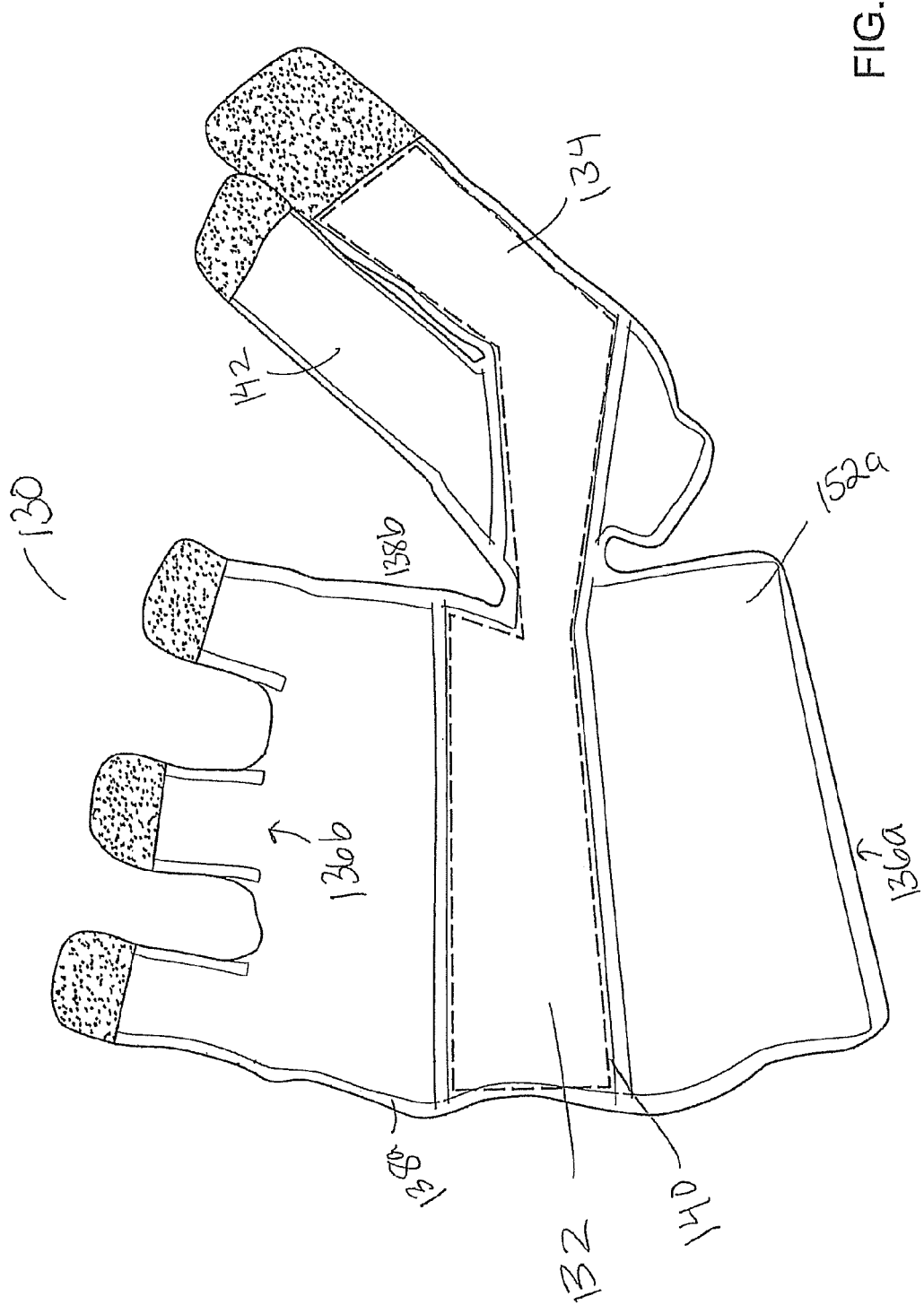
FIG. 12 is a perspective view of the interior surface of an exemplary lower leg wrap according to the subject invention illustrated in an unwrapped state.

Like the upper leg wrap 110, the lower leg and foot wrap 130 is formed of an interior surface 150a and exterior surface 152b joined along common peripheral edges to faun an inflatable chamber 140. In addition, the exterior surface 152b and interior surface 152a of the lower leg wrap 130 are made of non-elastic materials, which do not stretch when inflated, in order to facilitate localized compression of the lower leg 142 and foot 148. The lower leg wrap 130 may also be manufactured with a number of stitched darts 122 and gathers 124 (not shown) which are strategically placed to contour the lower leg and foot wrap 130 around the lower leg 142 and foot 148. The lower leg and foot wrap 130 may also include a permanent or detachable pressure gauge 121, (e.g. a manometer) and a pump 120 for inflating the compression apparatus 130. In one exemplary embodiment, the lower leg and foot wrap 130 is configured such that the inflatable chamber 140 is confined to only a portion of the lower leg and foot wrap 130. For example, the inflatable chamber 140 is illustrated in FIG. 12 by the area within the dotted lines. The exemplary inflatable chamber 140 is typically inflated with air, but may be filled with a number of different fluids including liquids and gels.

Figure 13A:
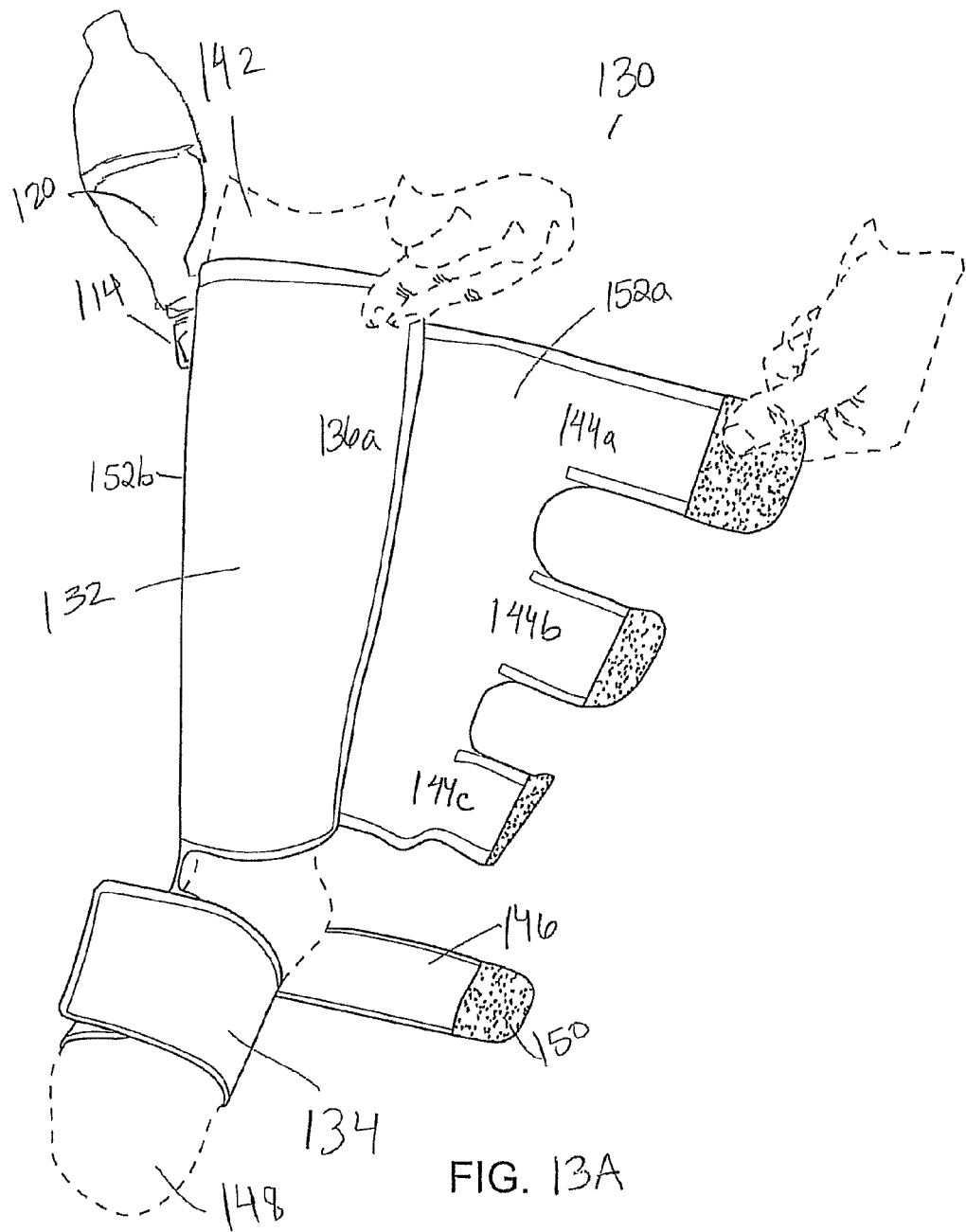
FIG. 13A is a perspective view of the exemplary lower leg wrap of FIG. 12 as it is being encircled around the lower leg of a patient.

Referring now to FIG. 13A, the lower leg and foot wrap 130 may be attached to by the patient to his or her lower leg 142 using one hand to hold vertical peripheral edge 136a in place, and encircling the upper portion 132 of the lower leg wrap 130 around the lower leg 142. The upper portion 132 of the lower leg and foot wrap 130 is then attached to itself along opposing vertical peripheral edges 136a and 136b using a number of connecting structures provided along vertical peripheral edge 136b, such as hook and loop fastening tabs 144a, 144b, and 144c. The structure and configuration of the connecting structures 144a-144c may also be varied, as described above with respect to fastening tabs 114a, 114b, and 114c of the upper leg wrap 110.

The lower portion 134 of the lower leg wrap 130 may have a number of configurations depending on the therapeutic needs of the patient. The lower portion 134 may be open-toed to expose the toes of the patient's foot 148 as shown in FIGS. 12A-12C. Alternatively, the lower portion 134 may be configured as a close-toed boot (not shown). In addition, the lower portion 134 may have an open heel as shown in FIGS. 13A-B or have a closed heel, similar to a boot (not shown).

Figure 13B:
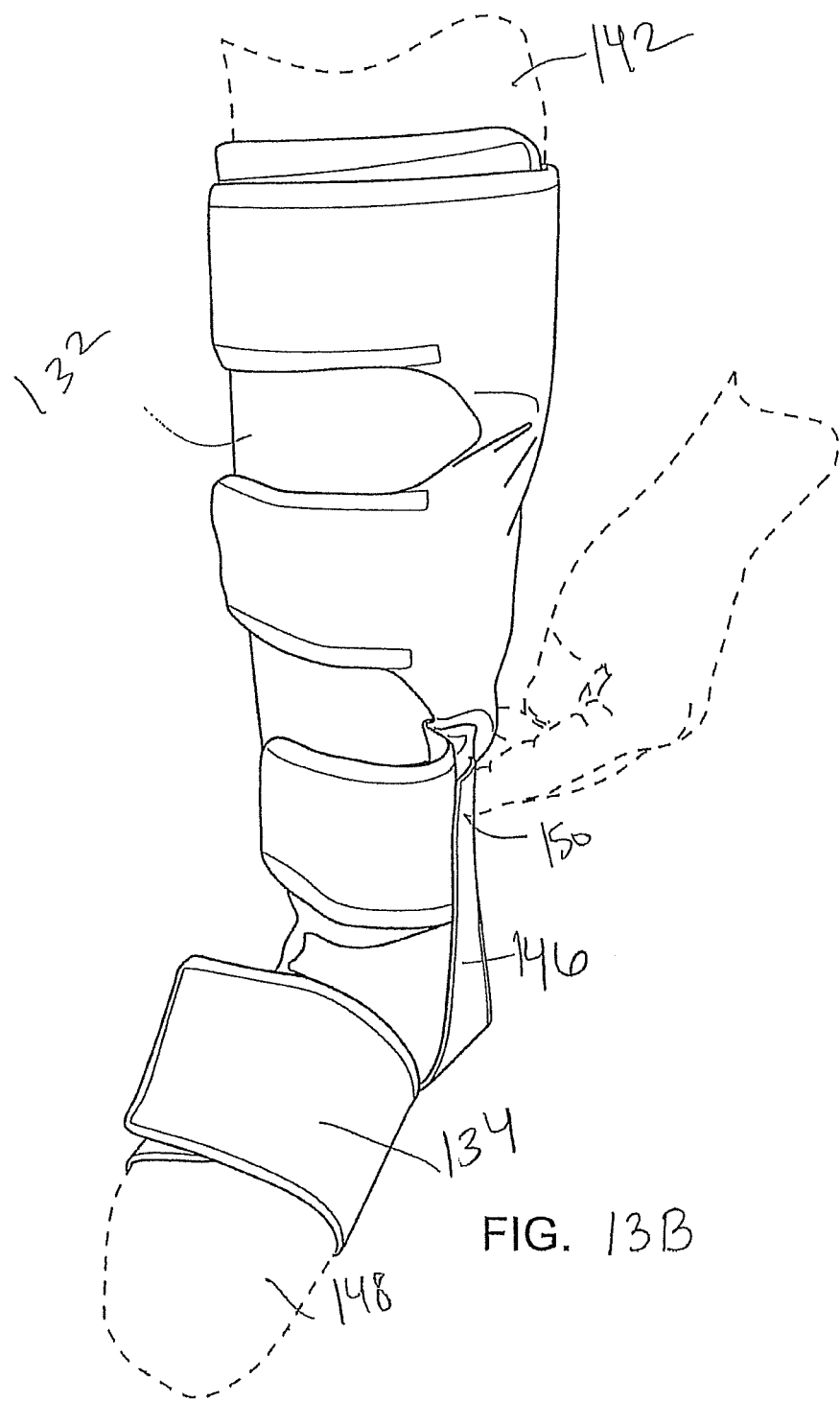
FIG. 13B is a perspective view of the exemplary lower leg wrap of FIG. 13A as the stirrup of the lower portion is being secured to the upper portion.

Referring now to FIG. 13B, a stirrup 146 may also be provided to help to secure the lower portion 134 in place. As shown in FIG. 12, the stirrup 146 is located between the upper portion 132 and the lower portion 134, and is typically one continuous piece of elastic material connected to and integrated with the lower portion 134. The stirrup 146 may have a hook and loop connecting tab 150, or other suitable connecting structure, to help secure the stirrup 146 to the upper portion 132.

While the subject invention of the present disclosure has been described with respect to preferred and exemplary embodiments, those skilled in the art will readily appreciate that various changes and/or modifications can be made to the invention without departing from the spirit or scope of the invention as described herein.

What is claimed is:

1. A venous closure catheter for performing sclerotherapy, comprising:
   a) an elongated catheter body having opposed proximal and distal end portions and at least one interior lumen;
   b) aperture means associated with the distal end portion of the catheter body and communicating with the at least one interior lumen of the catheter body for delivering a sclerosing solution into a saphenous vein; and
   c) abrading means operatively positioned on an exterior surface of the catheter body proximal to the aperture means for traumatizing an inner wall of the saphenous vein upon removal of the catheter body therefrom to promote closure of the saphenous vein after sclerotherapy,
   wherein the aperture means comprises a plurality of fluid delivery ports formed in the distal end portion of the catheter body.

2. A venous closure catheter as recited in claim 1, wherein the abrading means comprises a circumferential flange having a plurality of projections adapted and configured to abrade the inner wall of the saphenous vein.

3. A venous closure catheter as recited in claim 2, wherein the flange has a generally frusto-conical configuration having a base oriented toward the proximal end portion of the catheter body.

4. A venous closure catheter as recited in claim 2, wherein each projection has a barb-shaped configuration with a point that is oriented toward the proximal end portion of the catheter body.

5. A venous closure catheter as recited in claim 2, wherein the flange is adapted and configured for selective positioning along the length of the catheter body.

6. A venous closure catheter as recited in claim 2, wherein the flange is adapted and configured for selective positioning along the length of the catheter body.

7. A venous closure catheter for performing sclerotherapy, comprising:
   a) an elongated catheter body having opposed proximal and distal end portions, a fluid delivery lumen and a guidewire lumen;
   b) a plurality of discharge apertures associated with the distal end portion of the catheter body and communicating with the fluid delivery lumen of the catheter body for delivering a sclerosing solution into a saphenous vein; and
   c) a circumferential flange positioned on an exterior surface of the catheter body proximal to the discharge apertures and having a plurality of projections formed thereon for traumatizing an inner wall of the saphenous vein upon removal of the catheter body therefrom to promote closure of saphenous vein after sclerotherapy.

8. A venous closure catheter as recited in claim 7, wherein the flange has a generally frusto-conical configuration having a base oriented toward the proximal end portion of the catheter body.

9. A venous closure catheter as recited in claim 7, wherein each projection has a barb-shaped configuration with a point that is oriented toward the proximal end portion of the catheter body.

10. A method for performing sclerotherapy comprising:
    a) introducing an elongated venous catheter into a saphenous vein of a leg;
    b) delivering a sclerosing solution into the saphenous vein through a distal end portion of the venous catheter; and
    c) abrading the inner wall of the saphenous vein as the venous catheter is removed from the saphenous vein.

11. A method according to claim 10, further comprising the step of dividing the saphenous vein a short distance below the sapheno-femoral junction.

12. A method as recited in claim 11, further comprising the step of percutaneously introducing a guidewire into the saphenous vein at a location proximate the ankle and advancing the guidewire toward the divided end of the saphenous vein.

13. A method as recited in claim 12, wherein the step of introducing the venous catheter into the saphenous vein includes the step of guiding the introduction of the venous catheter along the guidewire from the divided end of the saphenous vein.

14. A method as recited in claim 11, further comprising the step of tying off the divided end of the sapheno-femoral junction with one or more sutures.

15. A method as recited in claim 10, further comprising the step of providing post operative pressure to the leg containing the abraded saphenous vein.

16. A method as recited in claim 15, further comprising the step of encircling the leg with a compression apparatus.

17. A method as recited in claim 16, wherein the step of encircling the leg with the compression apparatus further comprises the step of encircling at least an upper portion of the leg with a first wrap member.

18. A method as recited in claim 17, wherein the step of encircling the leg with the compression apparatus further comprises the step of encircling a lower portion of the leg and foot with a second wrap member.

19. A method as recited in claim 17, further comprising the step of securing the first wrap member about the upper portion of the leg using an adjustable strap around a patient's waist.

20. A method as recited in claim 16, further comprising the step of inflating a fluid chamber within a material of the compression apparatus.

21. A method as recited in claim 20, further comprising the step of measuring a pressure supplied to the leg by the inflated compression apparatus.

* * * * *